(12) United States Patent
Tearney

(10) Patent No.: US 7,313,432 B2
(45) Date of Patent: Dec. 25, 2007

(54) PHASE DISCRIMINATION FOR DETECTION OF VULNERABLE-PLAQUE

(75) Inventor: Guillermo J. Tearney, Cambridge, MA (US)

(73) Assignee: InfraReDx, Inc., Burlington, MA (US)

( * ) Notice: Subject to any disclaimer, the term of this patent is extended or adjusted under 35 U.S.C. 154(b) by 1045 days.

(21) Appl. No.: 10/269,698

(22) Filed: Oct. 11, 2002

(65) Prior Publication Data

US 2004/0073102 A1    Apr. 15, 2004

(51) Int. Cl.
*A61B 6/00*    (2006.01)
(52) U.S. Cl. ..................... 600/473; 600/475
(58) Field of Classification Search ............... 600/342, 600/473–477
See application file for complete search history.

(56) References Cited

U.S. PATENT DOCUMENTS

| | | | | |
|---|---|---|---|---|
| 5,687,730 A * | 11/1997 | Doiron et al. | ............... | 600/477 |
| 6,014,204 A * | 1/2000 | Prahl et al. | ................. | 356/73 |
| 6,294,775 B1 * | 9/2001 | Seibel et al. | ............. | 250/208.1 |
| 6,300,626 B1 * | 10/2001 | Brock et al. | ................. | 250/287 |
| 6,654,630 B2 * | 11/2003 | Zuluaga et al. | .............. | 600/476 |
| 2003/0028100 A1 * | 2/2003 | Tearney et al. | ............. | 600/431 |
| 2003/0191398 A1 * | 10/2003 | Motz et al. | .................. | 600/478 |
| 2004/0092830 A1 * | 5/2004 | Scott et al. | .................. | 600/478 |

* cited by examiner

*Primary Examiner*—Brian L. Casler
*Assistant Examiner*—Jacqueline Cheng
(74) *Attorney, Agent, or Firm*—Fish & Richardson P.C.

(57) ABSTRACT

A system for identifying vulnerable plaque includes an illumination subsystem for passing an illumination beam, modulated by a first modulation waveform, through a catheter. A receiving subsystem detects a collection beam, which is modulated by a second modulated waveform, from the catheter. A processing subsystem in communication with the receiving subsystem determines a relative phase difference between the first and second modulation waveforms.

41 Claims, 7 Drawing Sheets

PHASE DISCRIMINATION FOR DETECTION OF VULNERABLE-PLAQUE

FIELD OF INVENTION

This invention relates to the detection of vulnerable plaque within an arterial wall, and in particular, to detection of such plaques using near-infrared spectroscopy.

BACKGROUND

Lurking within the arterial wall of many seemingly healthy persons are one or more pools of lipid, referred to as vulnerable plaques. A fibrous cap covers the vulnerable plaque and separates its contents from the blood flowing in the lumen of the artery. Should this cap rupture, thrombogenic tissue will be exposed. This causes a cascade of blood clotting and thrombus formation that may occlude the artery. Depending on where this occurs, the result can be a sudden heart attack or stroke.

Because of the potentially devastating consequences of a vulnerable plaque, it is desirable to locate such plaques before the rupture of the fibrous cap. One method of doing so is to illuminate the wall of the artery with infrared light at a range of wavelengths and collecting the light reflected at each wavelength. If a vulnerable plaque is present, the spectrum obtained from the collected light will bear a characteristic signature.

There is, however, no guarantee that the collected light will have been reflected by structures within the arterial wall. In fact, a significant portion of the collected light is reflected not from within the arterial wall but from the blood or external to the wall itself. It is therefore desirable to discriminate between light reflected from within the arterial wall and all other light.

SUMMARY

The invention is based on the recognition that one can discriminate between those components of the collected light that have traversed long path lengths and those that have traversed short path lengths by observing phase and/or polarization differences between those components.

In one aspect, a system for identifying vulnerable plaque includes an illumination subsystem for passing an illumination beam through a catheter, the illumination beam being modulated by a first modulation waveform. A receiving subsystem detects a collection beam from the catheter. This detected collection beam is modulated by a second modulation waveform. A processing subsystem in communication with the receiving subsystem is configured to determine a relative path length traversed by the collection beam on the basis of the first and second modulation waveforms.

In one embodiment, the processing subsystem is configured to determine a relative path length traversed by the collection beam on the basis of a relative phase difference between the first and second modulation waveforms.

In another embodiment, the system includes a light source for generating the illumination beam. An optical modulator, in optical communication with the light source, impresses the first modulation waveform on the illumination beam. The light source can include an infrared light source. Examples of light sources include an arc lamp, a light-emitting diode, a super-luminescent diode, a wavelength-tunable light source, a broadband light source, and a laser. The light source can be a polarized or an unpolarized light source. The modulator can be an acousto-optical modulator, an electro-optic modulator, a Mach-Zehnder modulator, a laser-diode current modulator, or a phase-controlled rapidly scanning optical delay line.

In one embodiment, the receiving subsystem includes a detector disposed to intercept the collection beam and to generate a detected signal representative of the collection beam. Such a receiving subsystem can also include a phase-sensitive amplifier, in communication with the detector, for receiving the detected signal. The detector can be a single photodiode, a photocathode, a photo diode array, a photocathode array, a charge-coupled device array, a CMOS ("complementary metal oxide semiconductor") device array, or an array of charge-injection devices.

In another embodiment, the processing subsystem is configured to set a phase threshold and to reject a collection beam component when the difference between the phase of the second modulation waveform and the phase of the first modulation waveform is less than the phase threshold.

In another embodiment, the processing subsystem is configured to set a path length threshold and to reject a collection beam component when the difference between the path length traversed by the second modulation waveform and the path length of the first modulation waveform is less than the path length threshold In yet another embodiment, the system includes an optical fiber in optical communication with the light source for carrying the illumination beam. A first linear polarizer is in communication with the optical fiber. An optional polarization rotating element is in communication with the linear polarizer. The polarization rotating element can be, for example, a quarter-wave plate or a Faraday rotator.

The system can also include an additional optical fiber for carrying the collection beam and a second linear polarizer in communication with the additional optical fiber. The second linear polarizer is oriented to have a component orthogonal to the first linear polarizer.

In one embodiment, the illumination subsystem is configured to modulate the illumination beam by a plurality of first modulation waveforms and the receiving subsystem is configured to receive a collection beam modulated by a plurality of second modulated waveforms.

In another embodiment, the processing subsystem is configured to estimate an inverse transform of a signal present in the collection beam.

In yet another embodiment, the illumination subsystem is configured to generate an illumination beam at each of a plurality of wavelengths and to modulate each illumination beam with a plurality of modulation waveforms. The receiving subsystem is configured to detect a collection beam that includes components at a plurality of wavelengths, each of which is modulated by a plurality of modulation waveforms. The processing subsystem can then be configured to generate a phase or path length spectrum plot on the basis of data provided by the receiving subsystem. This includes estimating an inverse transform of a signal present in the collection beam.

In another aspect, a system for receiving light from an optical catheter includes first and second optical fibers extending through a catheter for guiding an illumination beam and a collection beam respectively. A first polarization filter is disposed in optical communication with the second optical fiber. A detector in communication with the second optical fiber generates a signal representative of the amplitude of the collection beam. A processor in communication with the detector collects data indicative of a difference between the collection beam and the illumination beam.

In one embodiment, the system includes a second polarization filter in optical communication with the first optical fiber. The second polarization filter is oriented to transmit a beam having a polarization orthogonal to that of the first polarization filter.

In another aspect of the invention, a system for receiving light from an optical catheter includes an optical fiber extending through the catheter for carrying an illumination beam and a collection beam, and a circular polarizer disposed in optical communication with the optical fiber. A detector in communication with the optical fiber generates a signal representative of the collection beam. This signal is provided to a processor in communication with the detector. The processor collects data indicative of a difference between the collection beam and the illumination beam.

The invention also includes a method for identifying vulnerable plaque. The method includes modulating an illumination beam with a first modulation waveform and passing the modulated illumination beam through a catheter. A collection beam is then recovered. As a result of having traversed a path through the artery, this collection beam has been modulated by a second modulation waveform. A relative phase difference between the first and second modulation waveforms is then determined.

In one practice, the method also include setting a phase threshold and rejecting a collection beam component when the difference between the phase of the second modulation waveform and the phase of the first modulation waveform is less than the phase threshold. In another practice, the method includes polarizing the illumination beam.

In another practice, the method includes setting a path length threshold and rejecting a collection beam component when the difference between the path length traversed by the second modulation waveform and the path length traversed by the first modulation waveform is less than the path length threshold.

Another aspect includes modulating the illumination beam with a plurality of first modulation waveforms. The inverse transform of a signal present in the collection beam can then be estimated.

Another practice of the invention includes providing an illumination beam having a plurality of components, each having a different wavelength. The illumination beam is then modulated by modulating each of the components with a plurality of first modulation waveforms, each having a different modulation frequency. The collection beam is recovered by recovering components at a plurality of wavelengths, each of which is modulated by a plurality of second modulation waveforms.

In another aspect, the invention includes a method for detecting a vulnerable plaque. The method includes illuminating an arterial wall with an illumination beam having a first polarization and recovering scattered light having a second polarization orthogonal to the first polarization. Scattered light having a second polarization parallel to the first polarization is then rejected. A vulnerable plaque is then detected on the basis of a difference between the illumination beam and the recovered scattered light.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

System Overview

Figure 1:
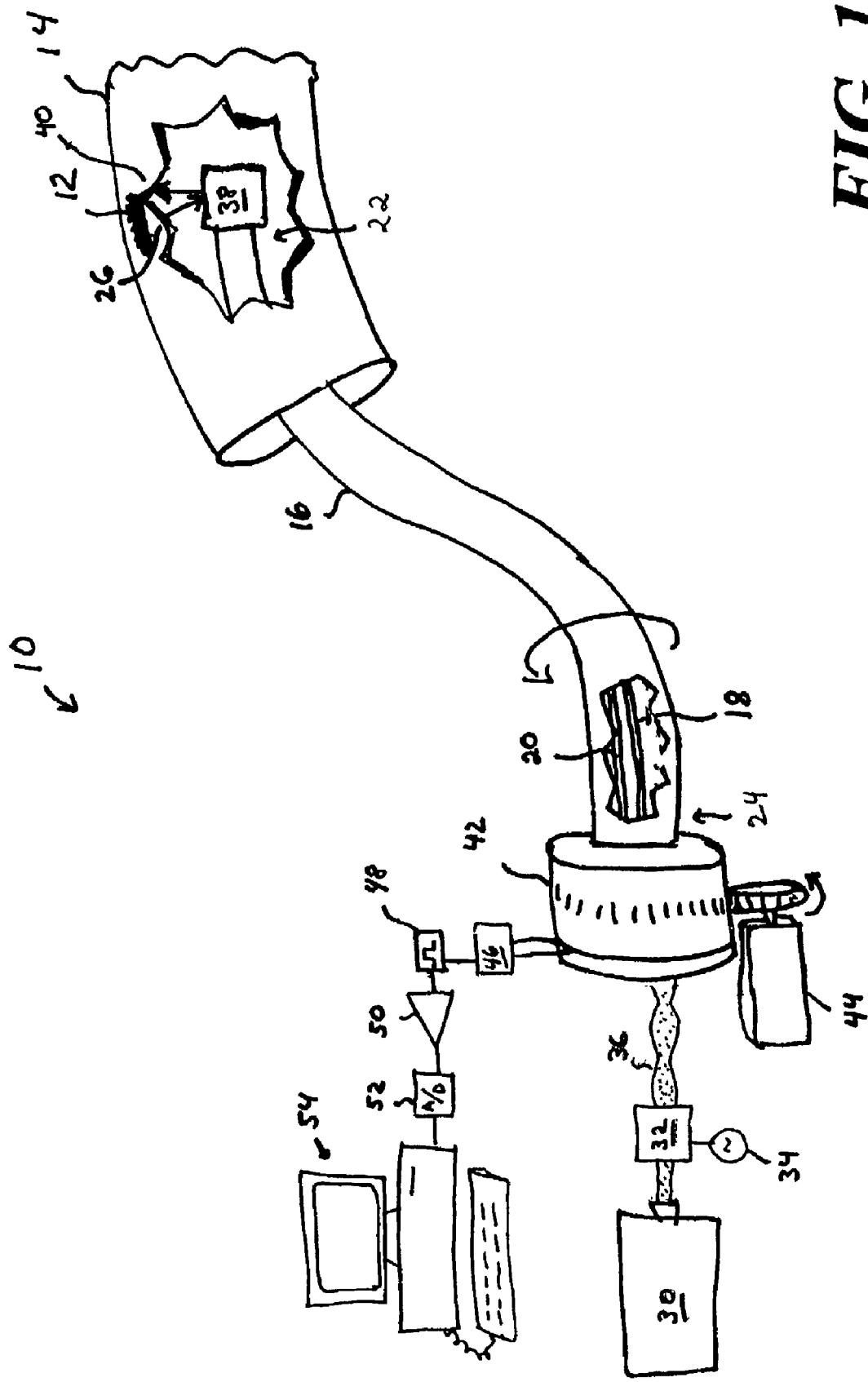
FIG. 1 shows a diagnostic system for identifying vulnerable plaque in an arterial wall of a patient.

FIG. 1 shows a diagnostic system 10 for identifying vulnerable plaque 12 in an arterial wall 14 of a patient. The diagnostic system features a catheter 16 to be inserted into a selected artery of the patient. A delivery channel 18 and a collection channel 20 extend between a distal end 22 and a proximal end 24 of the catheter 16. As shown in FIG. 1, the delivery channel 18 and collection channel 20 are on different optical fibers. However, the delivery channel 18 and the collection channel 20 can also share the same physical fiber. Alternatively, either the delivery channel 18, the collection channel 20, or both, can be distributed across multiple optical fibers.

Figure 2:
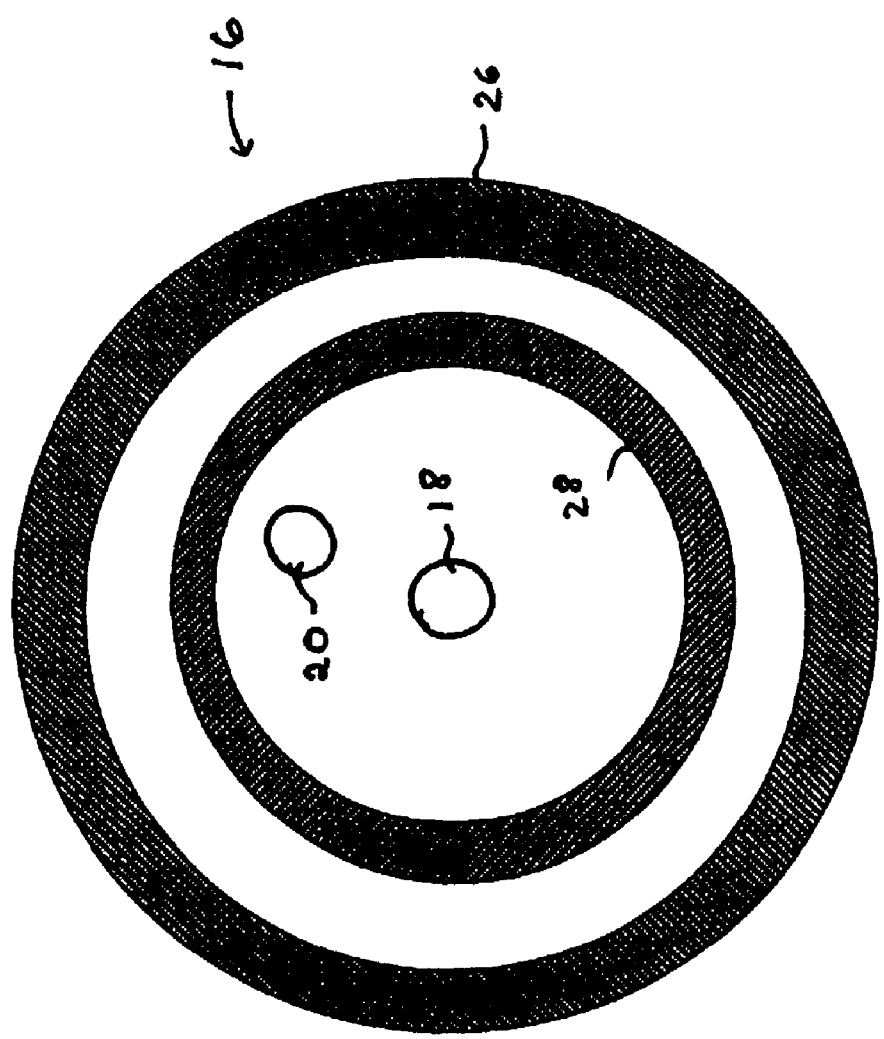
FIG. 2 is a cross-section of the catheter of FIG. 1.

As shown in FIG. 2, the catheter 16 includes a jacket 26 surrounding a rotatable torque cable 28. The delivery channel 18 extends along the center of a torque cable 28, and the collection channel 20 extends parallel to, but radially displaced from, the delivery channel 18. The rotatable torque cable 28 spins at rate between approximately 1 revolution per second and 400 revolutions per second.

Referring back to FIG. 1, the proximal end of the catheter 16 is in optical communication with an infrared laser 30. However, other infrared sources can also be used. For example, the source can be an arc lamp, a light-emitting diode, a super-luminescent diode, a wavelength-tunable light source, a broadband light source, or any infrared light source.

Light from the infrared laser 30 is coupled to an acousto-optical modulator 32 whose modulation frequency is controlled by an oscillator 34. However, other modulators can also be used to provide amplitude modulation of the light. Such modulators include electro-optic modulators, Mach-Zehnder modulators, and phase controlled rapidly scanning optical delay lines. Alternatively, the current feeding the laser diode can itself be modulated. The output of the modulator 32 is an illumination beam upon which is impressed a modulation waveform having a selected modulation frequency.

At the distal end of the catheter 16, a tip assembly 38 coupled to the torque cable 28 directs the illumination beam toward an illumination spot 40 on the arterial wall 14. The tip assembly 38 also collects light emanating from a collection volume and directs that light into the collection channel 20 to form a collection beam. An example of a tip assembly is that described in U.S. patent application Ser. No. 10/175, 479, entitled "MULTI-CHANNEL CATHETER TIP," the contents of which are herein incorporated by reference.

A multi-channel coupler 42 driven by a motor 44 engages a proximal end of the torque cable 28. When the motor 44 spins the multi-channel coupler 42, the coupler 42, the torque cable 28, and the tip assembly 38 spin together as a unit. This feature enables the diagnostic system 10 to circumferentially scan the arterial wall 14 with the illumination spot 40. An example of a multi-channel coupler 42 is that disclosed in U.S. patent application Ser. No. 10/164,721 filed on Jun. 7, 2002 and entitled "MULTI-CHANNEL OPTICAL COUPLER FOR SPINNING CATHETER," the contents of which are herein incorporated by reference.

In addition to spinning the torque cable 28, the multi-channel coupler 42 guides the modulated illumination beam into the delivery channel 18 and guides the collection beam emerging from the collection channel 20 into one or more detector subsystem 46. The detector subsystem 46 can be a single photodiode, a photocathode, or a one or two-dimensional array of photodiodes, photocathodes, charge-coupled devices, or CMOS ("complementary metal oxide semiconductor") devices, or charge-injection devices. The detector subsystem 46 is selected to have a response time that results in a 3 dB roll-off at a frequency that is greater than the modulation frequency.

To reduce the possibility of aliasing, a low-pass filter 48 having a pass-band extending to twice the Nyquist frequency of the modulation waveform filters an electrical signal generated by the detector subsystem 46. The output of the low-pass filter 48 is then provided to a phase-sensitive lock-in amplifier 50. The amplifier 50 outputs a signal that represents the average magnitude and phase of the time-varying electrical signal provided by the detector subsystem 46.

The amplifier output signal is provided to an analog-to-digital ("A/D") converter 52. The A/D converter 52 converts this signal into digital data that can be analyzed by a processor 54 to identify the presence of a vulnerable plaque 12 hidden beneath the arterial wall 14. Alternatively, lock-in quadrature phase detection can be performed by mixing the detected signal with an additional signal of the same or different frequency and detecting the DC component or beat frequency using a standard lock-in amplifier or by using a standard data-acquisition board.

Phase Discrimination

The processor 54 establishes a phase threshold to be compared with the phase of the modulated waveform impressed on the illumination beam. Different components of the illumination beam traverse different distances within the patient. Each component thus has a phase delay impressed upon it, the phase delay being dependent on the path length traversed by that component. The interior of the patient thus functions as a second modulator that impresses upon each component a second modulation waveform. In most cases, the second modulation waveform is a phase-shifted replica of the original modulation waveform imposed by the modulator 32.

If a component of the collection beam has, impressed upon it, a second modulation waveform having a phase delay, relative to the original modulation waveform, that is smaller than the phase threshold, the processor 54 recognizes that component as having failed to even reach the arterial wall 14. Only those components of the collection beam that return with a modulation waveform having a phase delay in excess of the phase threshold are ultimately used to form data representative of the spectrum of light returning from within the arterial wall 14.

The processor can also be configured to establish upper and lower phase thresholds. In this case, only those components of the collection beam that return with a modulation waveform having a phase delay between the upper and lower phase thresholds are ultimately used to form data representative of the spectrum of light returning from the arterial wall 14. The remaining components are rejected.

Alternatively, if the second modulation waveform indicates that the collection beam has traversed a path having a path length that is less than a path length threshold, the processor 54 likewise recognizes that component as having failed to even reach the arterial wall 14. Only those components of the collection beam that return with a modulation waveform indicating a path length in excess of the path length threshold are ultimately used to form data representative of the spectrum of light returning from within the arterial wall 14.

The processor can also be configured to establish upper and lower path length thresholds. In this case, only those components of the collection beam that return with a modulation waveform indicating that the component has traversed a path length between the upper and lower path length thresholds are ultimately used to form data representative of the spectrum of light returning from the arterial wall 14. The remaining components are rejected.

The phase threshold can be computed from theoretical calculations, such as using diffusion theory or Monte-Carlo modeling. Alternatively, the phase threshold can be determined in real-time by assessing the spectra for different phase delays and setting a phase threshold at a value at which the spectra change significantly.

Figure 3:
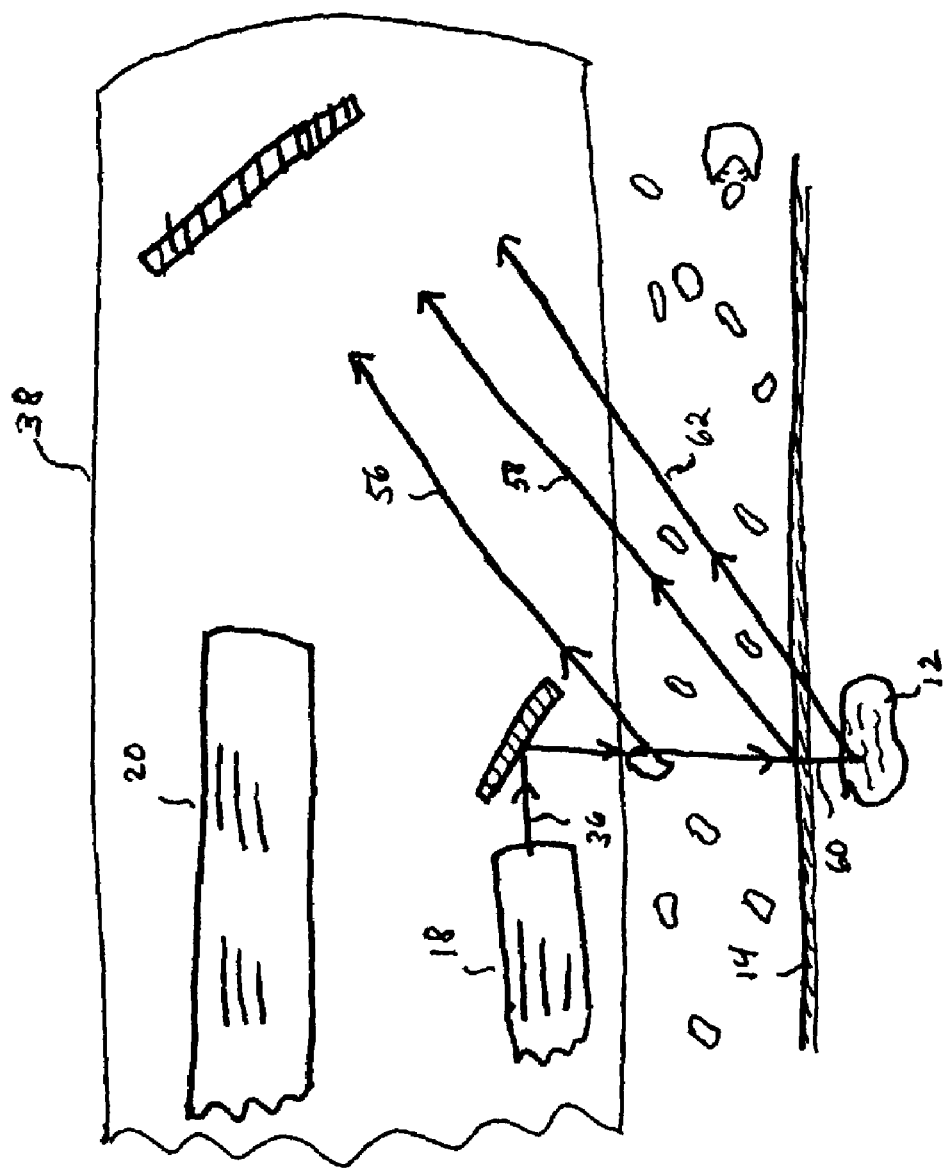
FIG. 3 illustrates scattering of light from various structure illuminated by the catheter of FIG. 1.

Referring to FIG. 3, when the illumination beam exits the delivery channel 18, it first encounters blood filling the artery's lumen. The blood reflects a first component 56 of the illumination beam into the collection channel 20. This first component 56 contains no useful information about structures within the arterial wall 14. A second component 58 of the illumination beam manages to traverse the blood, only to be reflected off the arterial wall 14. This second component 58 also contains no useful information about structures within the arterial wall 14. However, a third component 60 of the illumination beam manages to penetrate through the arterial wall 14. A great deal of this third component 60 is eventually absorbed within the wall 14 and is never seen again. However, a minuscule fraction of this third component 60, referred to herein as the fourth component 62, manages to escape from the wall 14, traverse the blood layer, and return to the collection channel 20. This fourth component 62 contains considerable information about structures within the arterial wall 14.

The light funneled into the collection channel 20 is thus a superposition of the first and second components 56, 58 and the fourth component 62. The first and second components 56, 58 represent noise, which must be rejected so that the information carried by the fourth component 62 can be recovered.

As noted above, the modulator 32 impresses, on the illumination beam, a modulation waveform having a selected frequency. As a result, the first, third and fourth components 56, 58, 62 will also be modulated at the same modulation frequency, but with different phase delays. The extent of the phase delay for each component will depend on the difference in path length between the various components. In particular, the fourth component 62, having traveled the longest distance, will have a longer phase delay than the first or second components 56, 58.

Additional sources of light, in addition to the three sources discussed above, are also present in the collection channel 20. In fact, the light in the collection channel 20 is a superposition of an infinite number of modulated components, each of which has a different phase delay in its modulation waveform. Each phase delay corresponds to a different path length traversed by that component. Each component is weighted by a value that depends on the path length traversed by that component. The signal carried by light present in the collection channel 20, hereafter referred to as the "collected signal," can thus be modeled as the Fourier transform of the remittance function R(L):

$$\int R(L) e^{-2jk_{mod}(\omega)L} dL$$

where R(L) is the remittance as a function of distance L along the path traversed by that light, $\omega$ is the modulation frequency, and $k_{mod}(\omega)$ is an experimentally determined effective wave number that depends on the modulation frequency and on the optical properties of the tissue through which the light passes. Representative procedures for obtaining $k_{mod}(\omega)$ are described in Pham, et al. "Broad bandwidth frequency domain instrument for quantitative tissue optical spectroscopy," Review of Scientific Instruments 71(6):2500-2513, 2000.

The signal provided by the amplifier 50, however, is $$I(\omega) = A(\omega) e^{j\phi(\omega)},$$

the amplitude of which is $$A(\omega) = |\int R(L) e^{-2jk_{mod}(\omega)l} dl|$$

and the phase of which is $$\phi(\omega) = arg(\int R(L) e^{-2jk_{mod}(\omega)L} dL)$$

A measurement I($\omega$) at a particular modulation frequency $\omega$ thus provides the processor 54 with one sample of the Fourier transform of the collected signal. If the light in the delivery channel 18 includes components modulated at several different modulation frequencies, one can then provide the processor 54 with samples of the collected signal at several different modulation frequencies. Using these samples, the processor 54 can evaluate the inverse Fourier transform $$\int I(\omega) e^{2jk_{mod}(\omega)} d\omega$$

and thereby recover the remittance function R(L). Once the remittance function is known, the processor 54 can integrate that function over an interval that excludes those values of L that correspond to light that failed to reach the interior of the arterial wall 14. This effectively excludes contributions from those components (such as the first and second components 56, 58) of the light present in the collection channel 20 that were reflected back from the blood or from the arterial wall 14. The phase of the resulting integral, or a value derived from that phase, can be used as the phase threshold. One example of a value derived from the phase is the remittance as a function of optical path length, R(L).

Phase Spectrum Map

Figure 4:
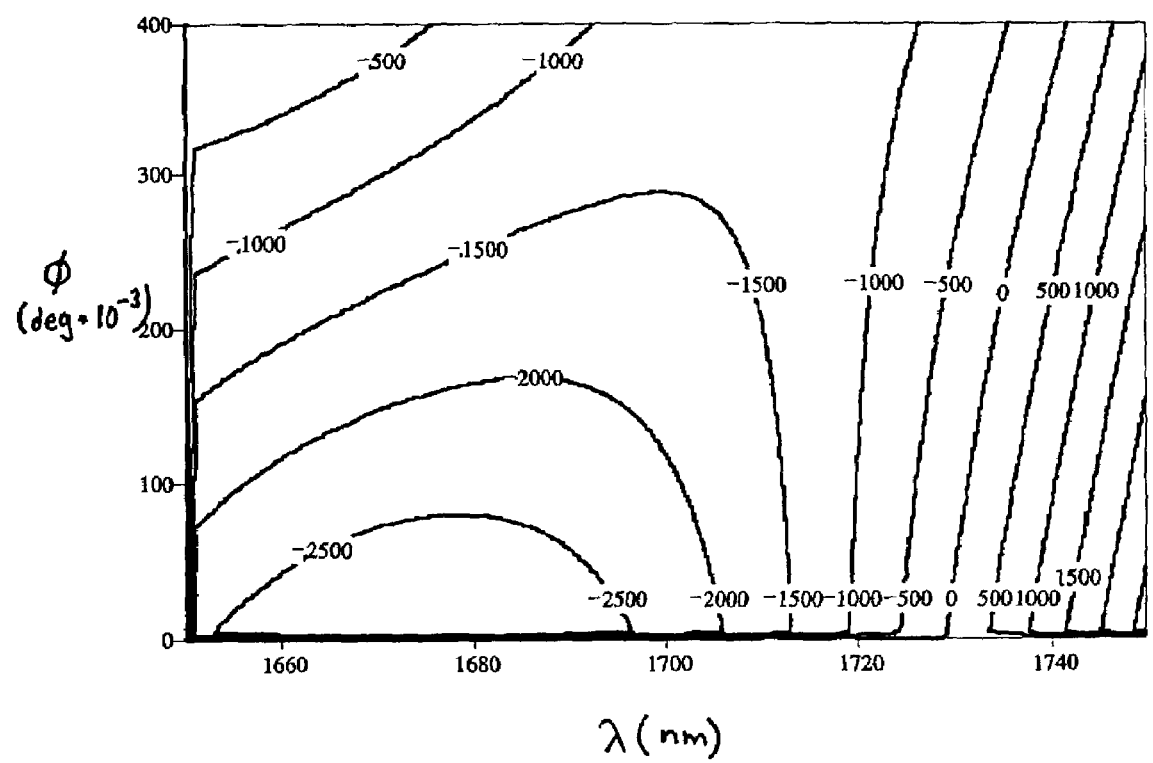
FIG. 4 is a contour plot showing exemplary contours of constant remittance.

The remittance function R(L) depends on both the path length L traversed by the light and the wavelength $\lambda$ of the light itself. As noted above, by modulating light having a particular wavelength at several modulation frequencies, it is possible to reconstruct the remittance function R(L) for that particular wavelength. By repeating this procedure at different wavelengths, one obtains a contour plot shown in FIG. 4. Since phase delay is a known function of path length, the vertical axis of the contour plot is shown as phase delay. However, since phase delay is an indicator of path length, the vertical axis can also indicate path length directly. The horizontal axis corresponds to different wavelengths of light. The numbers shown on each contour indicate the value of the remittance function at that contour relative to values of the remittance function at other contours. The phase spectrum plot is typically normalized to account for attenuation at the longer path lengths. This normalization is based on known attenuation constants for propagation of light in the blood.

A reference phase spectrum plot for a plaque-free artery can be derived on the basis of known optical properties of the blood and the arterial tissue. Alternatively reference phase spectrum plots can be obtained from clinical studies. A phase spectrum plot obtained from a patient can then be compared with one or more reference phase spectrum plots to identify features that suggest the presence of vulnerable plaque in the arterial wall 14 under examination.

Polarization Discrimination

Certain embodiments of the catheter 16 rely on the assumption that those components of the collection beam that have traversed the longest path are likely to have encountered many obstacles along that path. Since each encounter with an obstacle introduces a potential for a change in polarization, a collection-beam component that has traversed a long path is likely to have a polarization that is substantially different from that of the illumination beam. Conversely, a collection beam component that has traversed a short path is likely to have a polarization that is virtually identical to that of the illumination beam.

Figure 5:
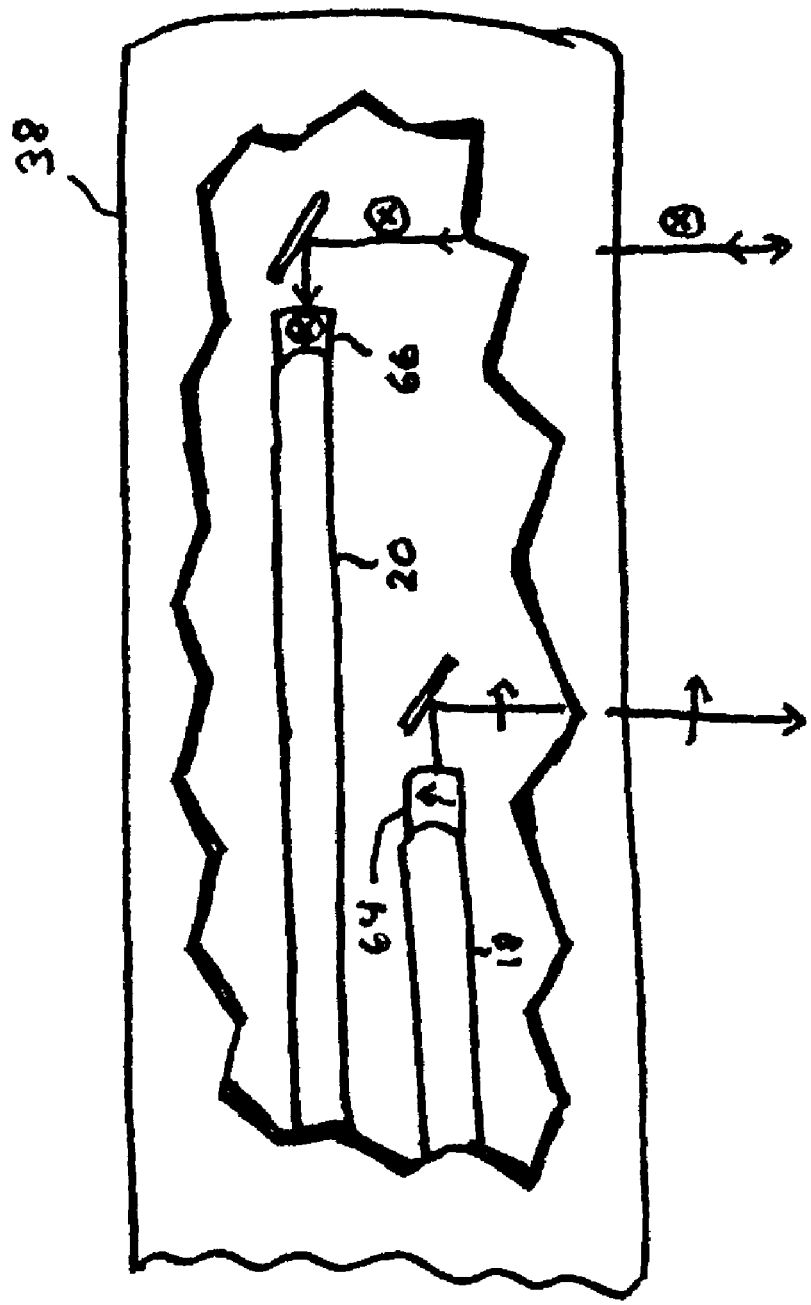
FIG. 5 is a distal tip of an embodiment that includes a polarizer.
Figure 6:
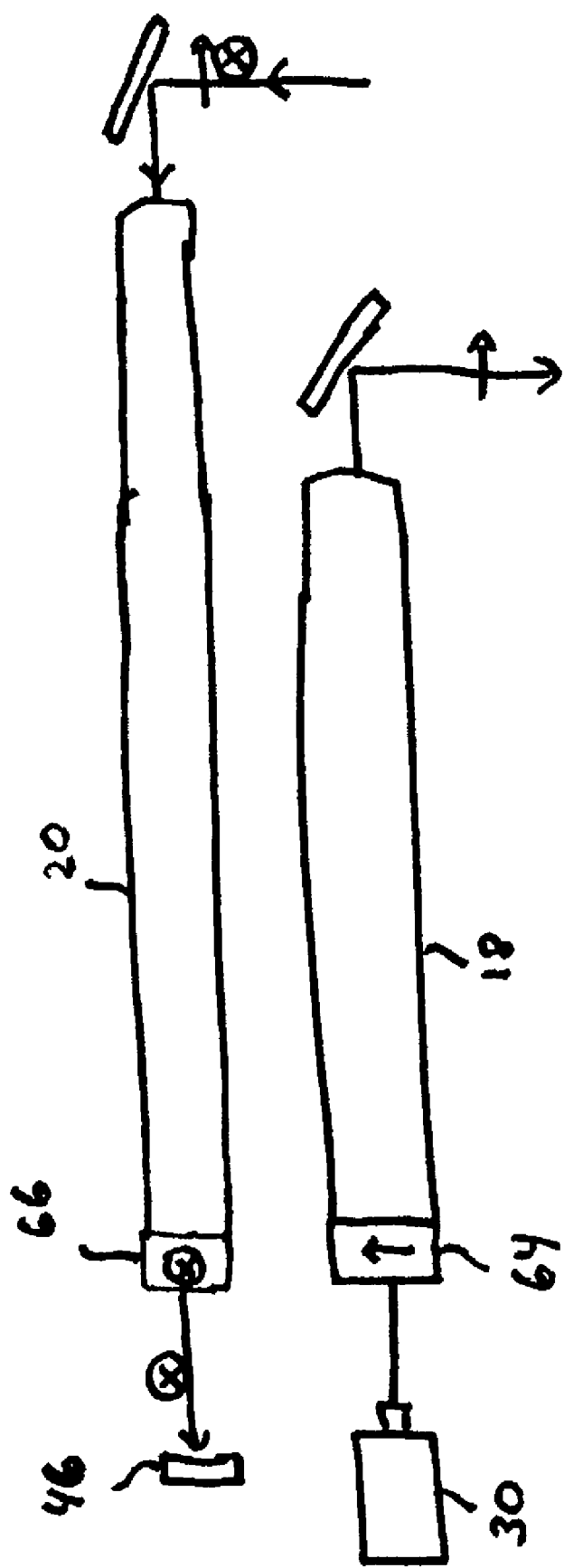
FIGS. 6 and 7 show embodiments that include an additional polarizer.
Figure 7:
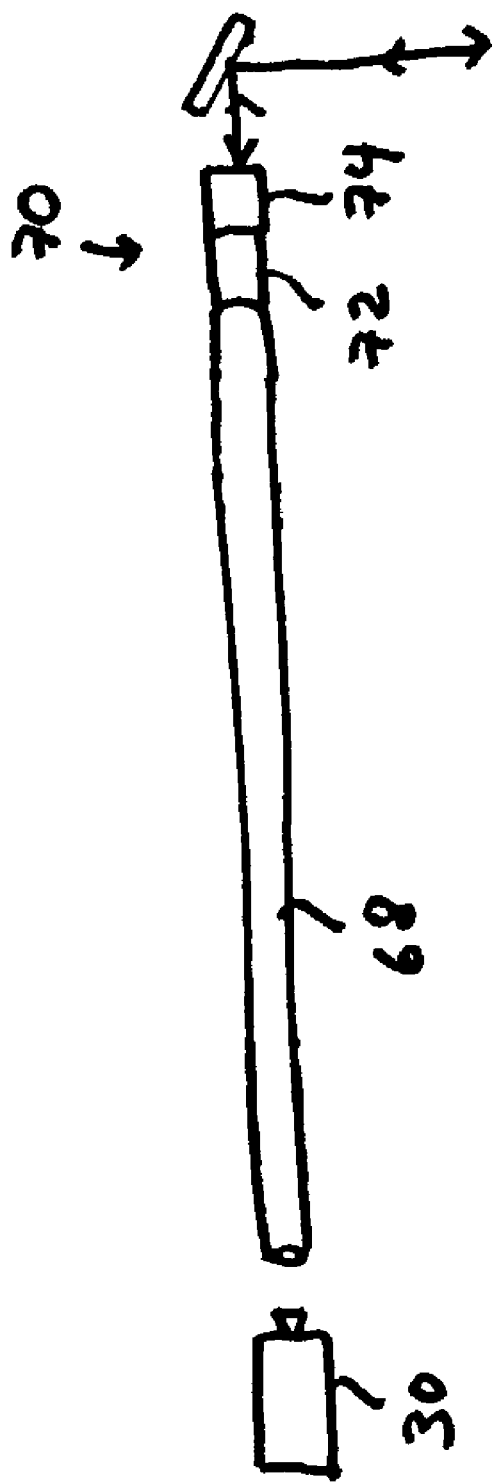

In recognition of this, certain embodiments of the catheter 16 are modified to provide a linearly polarized illumination beam and to collect only light that is orthogonally polarized relative to the illumination beam. For example, FIG. 5 shows a distal tip assembly 38 in which a first linear polarizer 64 is placed in the path of the illumination beam emerging from the distal face of the delivery channel 18. A second linear polarizer 66 is placed in the path of light entering the collection channel 20, either at its distal end, as shown in FIG. 6, or at its proximal end, as shown in FIG. 7. The second linear polarizer 66 is oriented such that its polarization axis is orthogonal to the polarization axis of the first linear polarizer 64.

In an alternative embodiment, shown in FIG. 6, the illumination beam is polarized at the source 30. This can be achieved either by using a source of polarized infrared light in conjunction with a polarization-preserving delivery channel 18 or by providing the first linear polarizer 64 at the proximal face of the polarization preserving delivery channel 18. In addition, the second linear polarizer 66 can be placed at the proximal end of the collection channel 20.

In yet another embodiment, shown in FIG. 7, a circular polarizer 70 is placed on the distal face of the single fiber 68. The circular polarizer 70 is made up of a linear polarizer 72 that contacts the distal face of the single fiber 68 and a quarter-wave plate 74 that contacts a distal face of the linear polarizer 72. When linearly polarized light exits the linear polarizer 72, its polarization is rotated forty-five degrees by the quarter-wave plate 74. On its return pass through the quarter-wave plate 74 the polarization of this light is rotated an additional forty-five degrees. Consequently, any light whose forty-five degree polarization remained unchanged will now be polarized by ninety degrees and will therefore be unable to pass through the linear polarizer 72 a second time.

In some embodiments, the circular polarizer 70 can be replaced by alternative polarizing elements that perform the same function. Examples of such elements include, but are not limited to a polarizing beam splitter, a Wollaston prism, or a Faraday element.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A system for identifying vulnerable plaque, the system comprising:
   an illumination subsystem for passing an illumination beam from through a catheter, the illumination beam being modulated by a first modulation waveform;
   a receiving subsystem for detecting a collection beam from the catheter, the collection beam having a plurality of collection beam components, each component being modulated by a corresponding second modulation waveform; and
   a processing subsystem in communication with the receiving subsystem, the processing subsystem being configured to determine a relative path length traversed by the components of the collection beam on the basis of the first and second modulation waveforms, the relative path length having utility in identifying vulnerable plaque.

2. The system of claim 1, wherein the processing subsystem is configured to determine a relative path length traversed by the collection beam on the basis of a relative phase difference between the first and second modulation waveforms.

3. The system of claim 1, wherein the illumination subsystem comprises:
   a light source for generating the illumination beam; and
   an optical modulator, in optical communication with the light source, for impressing the first modulation waveform on the illumination beam.

4. The system of claim 3, wherein the light source comprises an infrared light source.

5. The system of claim 3, wherein the light source is selected from the group consisting of an arc lamp, a light-emitting diode, a super-luminescent diode, a wavelength-tunable light source, a broadband light source, and a laser.

6. The system of claim 3, wherein the light source comprises a polarized light source.

7. The system of claim 3, wherein the modulator is selected from the group consisting of an acousto-optical modulator, an electro-optic modulator, a Mach-Zehnder modulator, a laser-diode current modulator, and a phase-controlled rapidly scanning optical delay line.

8. The system of claim 1, wherein the receiving subsystem comprises a detector disposed to intercept the collection beam and to generate a detected signal representative of the collection beam.

9. The system of claim 8, wherein the receiving subsystem further comprises a phase-sensitive amplifier in communication with the detector for receiving the detected signal.

10. The system of claim 8, wherein the detector is selected from the group consisting of single photodiode, a photocathode, a photodiode array, photocathodes, a charge-coupled device array, a CMOS ("complementary metal oxide semiconductor") device array, or an array of charge-injection devices.

11. The system of claim 1, wherein the processing subsystem is configured to set a phase threshold and to reject a collection beam component when the difference between the phase of the second modulation waveform and the phase of the first modulation waveform is less than the phase threshold.

12. The system of claim 1, wherein the processing subsystem is configured to set a first and second phase threshold and to reject a collection beam component when the difference between the phase of the second modulation waveform and the phase of the first modulation waveform is outside an interval between the first and second phase thresholds.

13. The system of claim 1, wherein the processing subsystem is configured to set a path length threshold and to reject a collection beam component when the difference between the path length traversed by the second modulation waveform and the path length traversed by the first modulation waveform is less than the path length threshold.

14. The system of claim 1, wherein the processing subsystem is configured to set a first and second path length threshold and to reject a collection beam component when the difference between the phase of the second modulation waveform and the phase of the first modulation waveform is outside an interval between the first and second path length thresholds.

15. The system of claim 1, further comprising
   an optical fiber in optical communication with the light source for carrying the illumination beam; and
   a first linear polarizer in communication with the optical fiber.

16. The system of claim 15, further comprising a polarization rotating element in communication with the linear polarizer.

17. The system of claim 16, wherein the polarization rotating element is selected from the group consisting of a quarter-wave plate and a Faraday rotator.

18. The system of claim 10, further comprising:
   an additional optical fiber for carrying the collection beam; and
   a second linear polarizer in communication with the additional optical fiber, the second linear polarizer being oriented to have a component orthogonal to the first linear polarizer.

19. The system of claim 15, wherein the optical fiber is a polarization-maintaining optical fiber.

20. The system of claim 1, wherein the illumination subsystem is configured to modulate the illumination beam by a plurality of first modulation waveforms and the receiving subsystem is configured to receive a collection beam modulated by a plurality of second modulated waveforms.

21. The system of claim 20, wherein the processing subsystem is configured to estimate an inverse transform of a signal present in the collection beam.

22. The system of claim 1, wherein
   the illumination subsystem is configured to generate an illumination beam at each of a plurality of wavelengths and to modulate each illumination beam with a plurality of modulation waveforms; and the receiving subsystem is configured to detect a collection beam that includes components at a plurality of wavelengths, each of which is modulated by a plurality of modulation waveforms.

23. The system of claim 22, wherein the processing subsystem is configured to generate a phase spectrum plot on the basis of data provided by the receiving subsystem.

24. The system of claim 22, wherein the processing subsystem is configured to generate a path length spectrum plot on the basis of data provided by the receiving subsystem.

25. The system of claim 22, wherein the processing subsystem is configured to estimate an inverse transform of a signal present in the collection beam.

26. A system for rejecting a component of received light from an optical catheter on the basis of a polarization state difference between an illumination component and the component of received light, the system comprising:
a first optical fiber extending through a catheter for guiding an illumination beam;
a second optical fiber extending through the catheter for guiding a collection beam;
a first polarization filter disposed in optical communication with the second optical fiber;
a detector in communication with the second optical fiber for generating a signal representative of the amplitude of the collection beam; and
a processor in communication with the detector for collecting data indicative of a polarization state difference between a component of the collection beam and the illumination beam and rejecting that component if the polarization state difference is less than a threshed, the polarization state difference having utility in identifying vulnerable plaque.

27. The system of claim 26, wherein the first optical fiber comprises a polarization preserving optical fiber.

28. The system of claim 26, further comprising a second polarization filter in optical communication with the first optical fiber, the second polarization filter being oriented to transmit a polarization orthogonal to that of the first polarization filter.

29. A system for determining a polarization state difference between a collection beam received from an optical catheter and an illumination beam, the system comprising:
an optical fiber extending through the catheter for an illumination beam and a collection beam;
a circular polarizer disposed in optical communication with the optical fiber;
a detector in communication with the optical fiber for generating a signal representative of the collection beam; and
a processor in communication with the detector for collecting data indicative of a difference between the polarization state of the collection beam and the polarization state of the illumination beam, the difference in polarization state having utility in identifying vulnerable plaque.

30. A method for identifying vulnerable plaque, the method comprising:
modulating an illumination beam with a first modulation waveform;
passing the modulated illumination beam through a catheter;
recovering a collection beam from the catheter, the collection beam having a plurality of collection beam components, each of which in modulated by a corresponding second modulation waveform; and
determining a path length traversed by the components of the collection beam on the basis of a difference between the first and second modulation waveforms, the path length having utility in identifying vulnerable plaque.

31. The method of claim 30, wherein determining a path length difference comprises determining a relative phase difference between the first and second modulation waveforms.

32. The method of claim 30, further comprising setting a phase threshold and rejecting a collection beam component when the difference between the phase of the second modulation waveform and the phase of the first modulation waveform is less than the phase threshold.

33. The method of claim 30, further comprising setting a path length threshold and rejecting a collection beam component when the difference between the path length traversed by the second modulation waveform and the path length traversed by the first modulation waveform is less than the path length threshold.

34. The method of claim 30, further comprising polarizing the illumination beam.

35. The method of claim 30, further comprising modulating the illumination beam with a plurality of first modulation waveforms.

36. The method of claim 35, further comprising estimating an inverse transform of a signal present in the collection beam.

37. The method of claim 30,
further comprising providing an illumination beam having a plurality of components, each having a different wavelength, and wherein
modulating an illumination beam comprises modulating each of the components with a plurality of first modulation waveforms, each having a different modulation frequency; and
recovering the collection beam comprises recovering a collection beam that includes components at a plurality of wavelengths, each of which is modulated by a plurality of second modulation waveforms.

38. The method of claim 37, further comprising generating a phase spectrum plot on the basis of information present in the collection beam.

39. The method of claim 37, further comprising generating a path length spectrum plot on the basis of information present in the collection beam.

40. The method of claim 37, further comprising estimating an inverse transform of a signal present in the collection beam.

41. A method for detecting a vulnerable plaque, the method comprising:
illuminating an arterial wall with an illumination beam having a first polarization;
recovering scattered light having a second polarization orthogonal to the first polarization;
rejecting scattered light having a second polarization parallel to the first polarization;
detecting a vulnerable plaque on the basis of a difference between the illumination beam and the recovered scattered light.

* * * * *